US 6,558,160 B2

(12) United States Patent
Schnaitter et al.

(10) Patent No.: US 6,558,160 B2
(45) Date of Patent: May 6, 2003

(54) ATTACHMENT DEVICE FOR INTRA-ORAL ORTHODONTIC APPLIANCE

(75) Inventors: Dwight P. Schnaitter, Englewood, CO (US); James D. Cleary, Glendora, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/912,766

(22) Filed: Jul. 25, 2001

(65) Prior Publication Data
US 2003/0022124 A1 Jan. 30, 2003

(51) Int. Cl.⁷ .................................................. A61C 7/00
(52) U.S. Cl. .......................................... 433/19; 433/22
(58) Field of Search ............................... 433/18, 19, 22

(56) References Cited

U.S. PATENT DOCUMENTS

| | | |
|---|---|---|
| 3,158,934 A | 12/1964 | Waldman |
| 3,508,332 A | 4/1970 | Armstrong .................... 433/21 |
| 3,690,003 A | 9/1972 | Gerber ......................... 433/19 |
| 3,798,773 A | 3/1974 | Northcutt |
| 4,462,800 A | 7/1984 | Jones .......................... 433/19 |
| 4,551,095 A | 11/1985 | Mason ......................... 433/19 |
| 4,583,944 A | 4/1986 | Hanson ........................ 433/22 |
| 4,795,342 A | 1/1989 | Jones .......................... 433/19 |
| 5,120,218 A | 6/1992 | Hanson ........................ 433/19 |
| 5,183,388 A | 2/1993 | Kumar ......................... 433/19 |
| 5,306,142 A | 4/1994 | Richards ...................... 433/22 |
| 5,352,116 A | 10/1994 | West ........................... 433/19 |
| 5,545,037 A | 8/1996 | Takeshi ........................ 433/21 |
| 5,562,445 A | 10/1996 | DeVincenzo et al. ......... 433/19 |
| 5,651,672 A | 7/1997 | Cleary et al. ................. 433/19 |
| 5,711,667 A | 1/1998 | Vogt ............................ 433/19 |
| 5,718,576 A * | 2/1998 | Schnaitter et al. ............ 433/22 |
| 5,738,514 A * | 4/1998 | DeVincenzo et al. ......... 433/19 |
| 5,752,823 A * | 5/1998 | Vogt ............................ 433/19 |
| 5,829,975 A * | 11/1998 | Gold ............................ 433/19 |
| 5,964,588 A | 10/1999 | Cleary ......................... 433/19 |
| 5,980,247 A | 11/1999 | Cleary ......................... 433/19 |
| 6,053,730 A | 4/2000 | Cleary ......................... 433/19 |
| 6,120,289 A * | 9/2000 | Cleary et al. ................. 433/19 |

OTHER PUBLICATIONS

Pending U.S. patent application Ser. No. 09/687,392, filed Oct.13, 2000.
Pending U.S. patent application Ser. No. 09/912,911, filed Jul. 25, 2001.
Jasper Jumper Color Atlas, by Franz–Peter Schwindling, pp. 31–39, 78–81, 85–89, 1997.
Jasper Jumper manual, American Orthodontics, date unknown.

* cited by examiner

Primary Examiner—Cary E. O'Connor
(74) Attorney, Agent, or Firm—James D. Christoff

(57) ABSTRACT

An orthodontic attachment device connects an intra-oral appliance to other orthodontic components in the oral cavity. The attachment device is particularly useful for telescoping-type interarch appliances that tend to reposition one dental arch relative to the other dental arch. The attachment device includes a first section that is non-rotatably connected to an archwire, and a second section that has an opening. The opening of the second section pivotally receives a coupler of the interarch appliance.

25 Claims, 8 Drawing Sheets

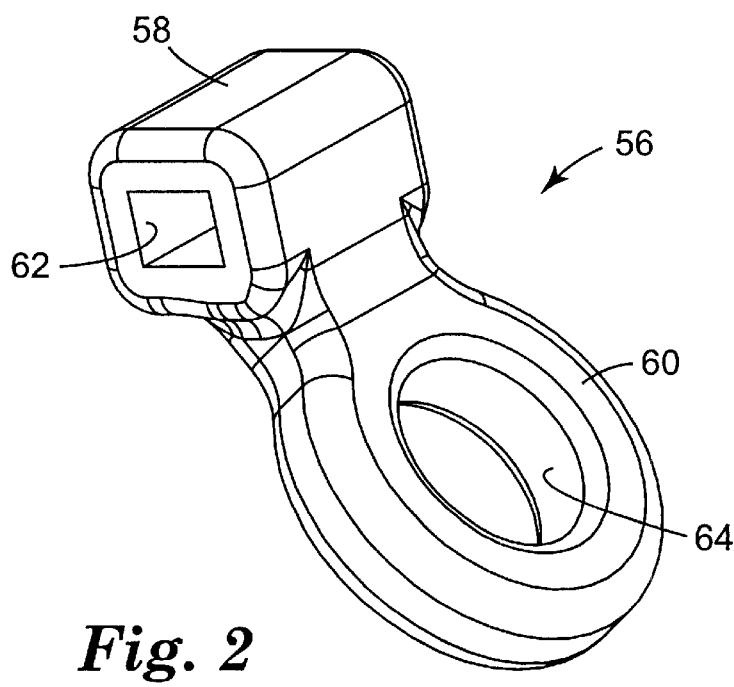
*Fig. 2*
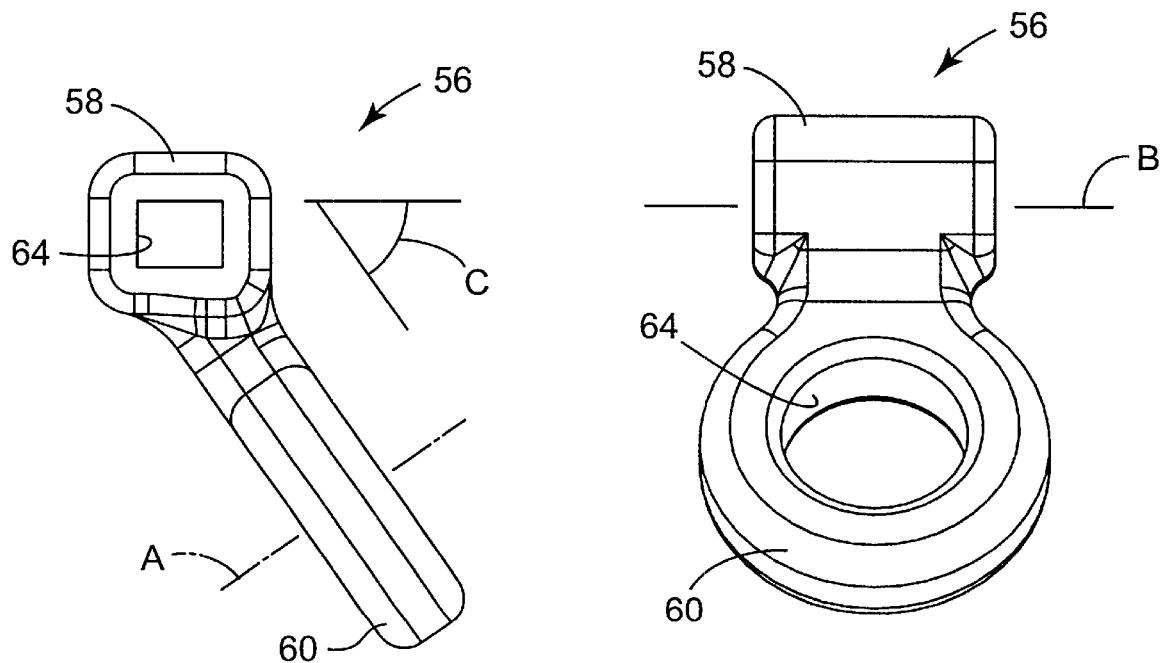
*Fig. 3*  *Fig. 4*

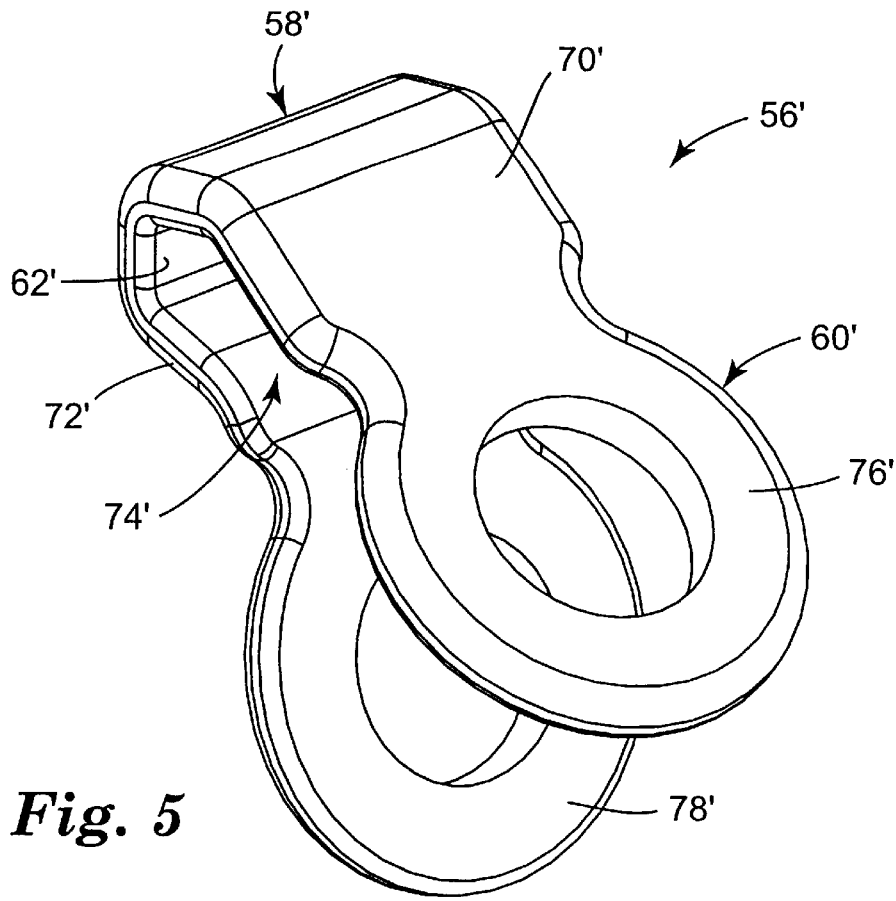
*Fig. 5*
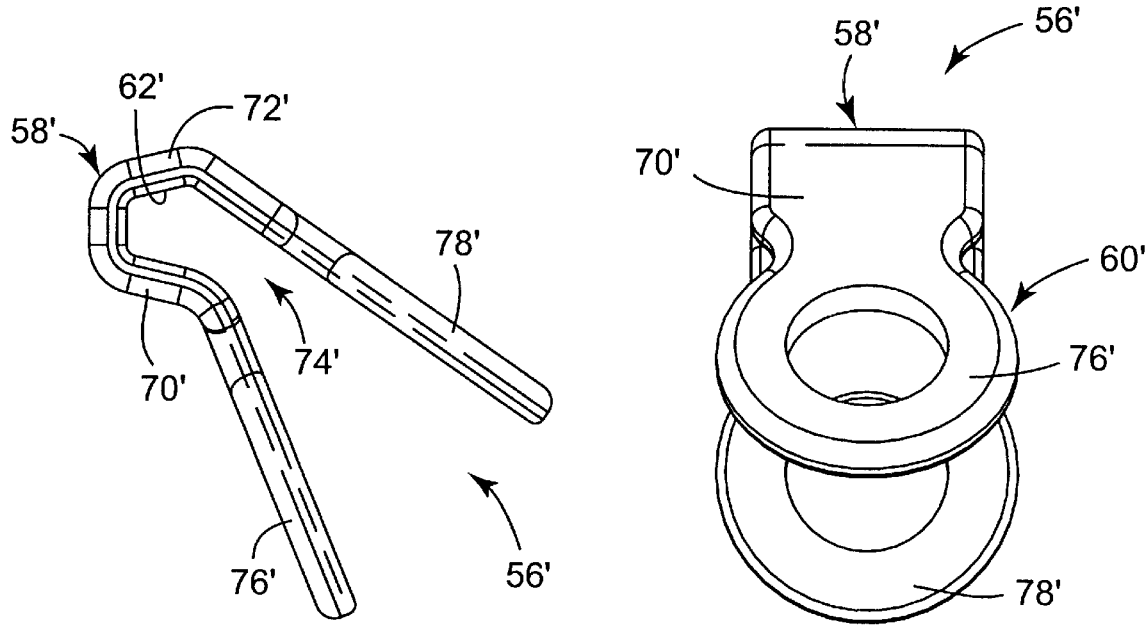
*Fig. 6*  *Fig. 7*

ATTACHMENT DEVICE FOR INTRA-ORAL ORTHODONTIC APPLIANCE

BACKGROUND OF THE INVENTION

1. Field of the Invention

This invention relates to a device that is used in the course of orthodontic treatment. More particularly, the present invention relates to an attachment device for connecting an interarch appliance to other orthodontic components in the patient's oral cavity.

2. Description of the Related Art

Orthodontic treatment involves movement of malpositioned teeth to orthodontically correct locations. Orthodontic treatment can improve the patient's occlusion so that the teeth of one jaw function in a satisfactory manner in cooperation with the teeth of the opposite jaw. In addition, teeth that are straightened by orthodontic treatment can significantly improve a patient's facial appearance.

One type of orthodontic treatment includes the use of a system of tiny appliances known as brackets. The brackets are connected to anterior, cuspid and bicuspid teeth, and an archwire is placed in a slot of each bracket. The archwire forms a track to guide movement of the brackets and the associated teeth to desired positions for correct occlusion. Typically, the ends of the archwire are received in appliances known as buccal tube brackets that are secured to molar teeth.

The orthodontic treatment of some patients includes correction of the alignment of the upper dental arch with the lower dental arch. For example, certain patients have a condition referred to as a Class II malocclusion where the lower dental arch is located an excessive distance in a rearward direction relative to the location of the upper dental arch when the jaws are closed. Other patients may have an opposite condition referred to as a Class III malocclusion wherein the lower dental arch is located in a forward direction of its desired location relative to the position of the upper dental arch when the jaws are closed.

Orthodontic treatment of Class II and Class III malocclusions are commonly corrected by movement of the upper dental arch as a single unit relative to the movement of the lower dental arch as a single unit. To this end, forces are often applied to each dental arch as a unit by applying force to the brackets, the buccal tubes or the archwires, or attachment devices connected to the brackets, buccal tubes, or archwires. In this manner, a Class II or Class III malocclusion can be corrected at the same time that the archwires and the brackets are used to move individual teeth to desired positions relative to each other.

A number of appliances are known in the art for correcting Class II and Class III malocclusions. For example, the appliances described in U.S. Pat. Nos. 3,798,773, 4,462,800 and 4,551,095 are made of telescoping tube assemblies that urge the dental arches toward positions of improved alignment. The telescoping tube assemblies are securely coupled to other orthodontic components in the oral cavity such as brackets, buccal tubes or archwires.

Another type of telescoping tube appliance for repositioning the dental arches is described in U.S. Pat. No. 5,964,588. The appliance described in this patent has a spring that urges telescoping members away from each other to achieve desired movement of the patient's teeth. Other patents that describe orthodontic telescoping tube appliances with springs include U.S. Pat. Nos. 5,711,667 and 5,562,445.

The telescoping tube appliance that is described in U.S. Pat. No. 5,964,588 has a connector on each end. In one embodiment described in this patent, an upper connector has a hole that receives a pin with a shank having a generally "L"-shaped configuration. The shank of the pin is of a size that is adapted to fit in the passage of a buccal tube, a headgear tube or other orthodontic appliance that is fixed to the upper dental arch. A lower connector includes a pair of opposed arms that are bendable toward each other to a closed position in order to connect to an archwire, an auxiliary wire or another component that is secured to the patient's lower dental arch.

While the concepts described in U.S. Pat. No. 5,964,588 are generally satisfactory, there is a continuing need in the art for improvements that facilitate the installation and use of the interarch appliance. Preferably, any such improvements would also increase the versatility of the appliance so that it can be adapted for use in a variety of different situations with different patients. Moreover, it is preferable that any such improvements do not increase the cost of the appliance or increase the likelihood that the patient will experience discomfort during the course of treatment.

SUMMARY OF THE INVENTION

The present invention relates to an attachment device for orthodontic interarch appliances that reposition the lower dental arch relative to the upper dental arch. The attachment device is connected to the archwire and extends outwardly from the tooth structure. The attachment device includes an opening that receives a coupler of the interarch appliance and enables the interarch appliance to pivot during opening and closing movements of the patient's jaws.

The attachment device of the present invention is easy to install and allows the practitioner to readily connect or disconnect the interarch appliance as needed. The attachment device holds the interarch appliance in a position that avoids interference between the appliance and the brackets that are mounted on the patient's adjacent teeth. The attachment device also holds the interarch appliance in an orientation that reduces the likelihood of excessive contact between the interarch appliance and the patient's soft tissue, with the result that the patient experiences less discomfort in use.

In more detail, the present invention is directed in one embodiment to an orthodontic assembly. The assembly comprises an orthodontic system that includes a set of brackets and an elongated archwire connected to the brackets. The assembly also comprises an interarch appliance for repositioning the lower dental arch relative to the upper dental arch. The interarch appliance includes a coupler having an arm. The assembly also comprises an attachment device that is connected to the orthodontic system. The attachment device includes a body having a first section and a second section. The first section has a passage receiving the archwire. The first section is substantially non-rotatable relative to the archwire in directions about the length of the archwire. The second section includes an opening that pivotally receives the arm of the coupler.

Another aspect of the present invention is directed toward an orthodontic attachment device. The device comprises a body having a first section and a second section connected to the first section. The first section has a passage with a central axis and a generally rectangular cross-sectional configuration in reference planes perpendicular to the central axis for non-rotatably receiving an archwire. The second section extends away from the central axis in a generally perpendicular direction and has an opening. The second section includes a peripheral edge segment surrounding the opening for connection to an appliance.

The present invention is also directed to a method of connecting a dental arch repositioning appliance to an orthodontic system that includes a set of brackets and an elongated archwire connected to the brackets. The method includes the act of placing an archwire in a passage of an attachment device in an orientation such that the device generally extends outwardly from the archwire. The method also comprises the act of coupling the device to the archwire such that the device is substantially non-rotatable relative to the longitudinal axis of the archwire. The method further comprises the act of pivotally connecting an outer section of the device to the repositioning appliance.

The present invention provides an important solution to the problem of connecting an orthodontic interarch appliance to a patient's dental arch in a relatively short period of time so that the time that the patient spends in the chair is minimized. Advantageously, the present invention avoids the need to connect the interarch appliance to a buccal tube bracket as in past practice, an advantage in instances where the buccal tube does not include an extra passage for receiving an auxiliary wire or appliance.

If desired, both the attachment device and the interarch appliance may be constructed so that they are universally adaptable for use on either the right side or the left side of the patient's dental arch. As such, manufacturing costs as well as the size of the practitioner's inventory of orthodontic components can be reduced. Moreover, such construction can result in fewer errors in installing the interarch appliance in the dental operatory.

These and other aspects of the invention are described in more detail below and are illustrated in the accompanying drawings.

BRIEF DESCRIPTION OF THE DRAWINGS

FIG. 2 is an enlarged perspective view of the attachment device alone that is shown in FIG. 1;

FIG. 3 is a reduced end elevational view of the attachment device depicted in FIG. 2;

FIG. 4 is a reduced front elevational view of the attachment device shown in FIGS. 2–3;

FIG. 5 is an enlarged perspective view of an attachment device according to another embodiment of the invention;

FIG. 6 is an end elevational view of the attachment device shown in FIG. 5;

FIG. 7 is a front elevational view of the attachment device shown in FIGS. 5–6;

DETAILED DESCRIPTION OF THE PREFERRED EMBODIMENTS

Figure 1:
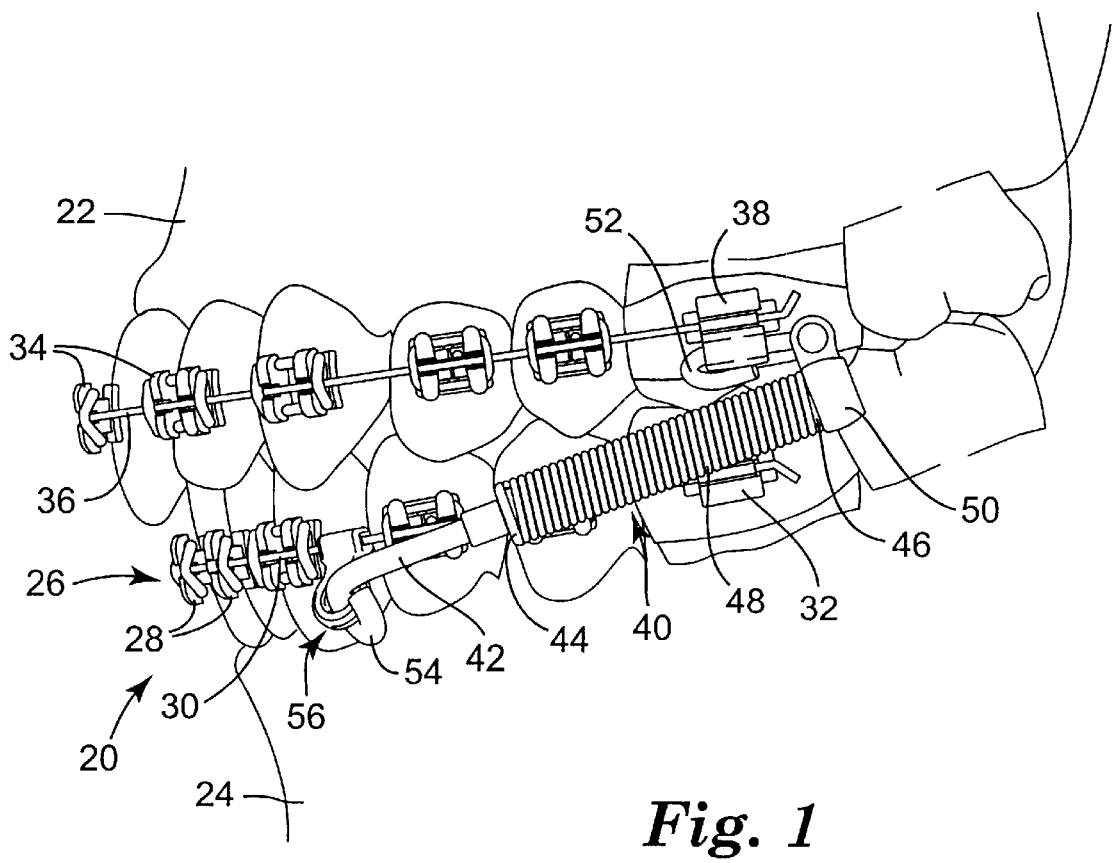
FIG. 1 is a side elevational view of an exemplary upper and lower dental arch of a patient undergoing orthodontic treatment utilizing an orthodontic assembly that includes an attachment device according to one embodiment of the present invention.

An orthodontic assembly according to one embodiment of the invention is illustrated in FIG. 1 and is broadly designated by the numeral 20. In FIG. 1, the assembly 20 is mounted on an exemplary upper dental arch 22 and an exemplary lower dental arch 24 of a patient that is undergoing orthodontic treatment.

The assembly 20 includes an orthodontic system 26. The system 26 includes a set of lower orthodontic brackets 28 that are mounted on teeth of the lower dental arch 24. An elongated lower archwire 30 extends through slots of the lower brackets 28 as well as through a passage of a lower buccal tube 32 that is received on a molar tooth of the patient's lower dental arch 24. The archwire 30 is secured to the brackets 28 by elastomeric O-ring ligatures in the drawings, although other types of ligatures could be used as well.

The orthodontic system 26 also includes a set of upper brackets 34 that are affixed to teeth of the patient's upper dental arch 22. An upper archwire 36 extends through slots of the upper brackets 34. The upper archwire 36 also extends through a passage of an upper buccal tube 38 that is secured to a molar tooth of the patient's upper dental arch 22. In this example, elastomeric O-ring ligatures are also used to couple the upper archwire 36 to the upper brackets 34.

The orthodontic assembly 20 also includes an interarch appliance 40 for repositioning the lower dental arch 24 relative to the upper dental arch 22. The interarch appliance 40 is preferably a telescoping-type of appliance that exerts a force on the patient's jaws when the jaws are closed for correction of a Class II or Class III malocclusion. In the illustrated example, the force provided by the interarch appliance 40 tends to move the lower dental arch 24 in a forwardly direction relative to the upper dental arch 22 to correct a Class II malocclusion. However, and as will be explained in more detail in the paragraphs that follow, the appliance may also be an appliance for correcting a Class III malocclusion or for closing the space that remains after extraction of a tooth or teeth.

Preferably, the interarch appliance 40 includes a first member 42, a second member 44 and a third member 46. The second member 44 has a tubular configuration and slidably receives a portion of the first member 42. The third member 46 also has a tubular configuration and slidably receives a portion of the second member 44.

Preferably, the interarch appliance 40 includes a spring such as the coil spring 48. In this embodiment, the spring 48 extends between opposite ends of the second and third members 44, 46 and urges the second and third members 44, 46 in directions away from each other. The first member 42 is freely slidable within the second member 44, although other constructions are also possible.

The interarch appliance 40 is preferably similar to the force module appliance described in U.S. Pat. No. 5,964,588 which is incorporated by reference herein. The reader is referred to that patent for additional information regarding other features and options of the appliance 40 if desired.

The third member 46 includes an upper connector 50 for coupling the interarch appliance 40 to the components of the orthodontic system 26 that are mounted on the patient's upper dental arch 22. The connector 50 has a hole that receives a pin 52 with an enlarged head on one end. The pin 52 includes a shank that is bent to an angle of approximately 90 degrees, and the shank extends through a passage of the upper buccal tube 38. An outer end of the pin 52 remote from the head is bent in an arc in order to secure the pin 52 to the buccal tube 38.

The interarch appliance 40 also includes a lower connector 54 for coupling the appliance 40 to the components of the orthodontic system 26 that are mounted on the patient's lower dental arch 24. The lower connector 54 is preferably integrally connected to the first member 42 and has an arm with a generally loop-shaped or hook-shaped configuration. Optionally, the connector 54 is formed by annealing an elongated wire body that also includes the first member 42 and then bending the outer end section of the body to a generally "C"-shaped loop. The loop is preferably left in a slightly open orientation until such time as the interarch appliance 40 is installed in the patient's oral cavity. The loop is then crimped to a closed position with a pair of dental pliers or other hand instrument.

The orthodontic assembly 20 also includes an attachment device 56 for pivotally coupling the interarch appliance 40 to the orthodontic system 26. The attachment device 56 is shown in more detail in FIGS. 2–4, and includes a body having a first section 58 and a second section 60. In this embodiment, the first section 58 and the second section 60 are integrally made as a single unitary component, although other constructions are also possible.

The first section 58 of the attachment device 56 includes a passage 62 for receiving the lower archwire 30. The passage 62 has a central axis, and preferably has a rectangular configuration in reference planes that are perpendicular to the central axis as shown in FIGS. 2 and 3. Preferably, the rectangular configuration is adapted to matingly receive a segment of an archwire (such as the lower archwire 30) having a complementary rectangular cross-sectional configuration.

The second section 60 of the attachment device 56 extends outwardly from the central axis of the passage 62 in a lateral direction. The second section 60 includes an opening 64 that is completely surrounded by a peripheral inner edge segment of the second section 60. The opening 64 is preferably circular, although other shapes are also possible.

The opening 64 has a central axis that is indicated by the letter "A" in FIG. 3. Preferably, but not necessarily, the axis "A" is perpendicular to the central axis of the passage 62 and does not intersect with the central axis of the passage 62. The central axis of the passage 62 is indicated by the letter "B" in FIG. 4.

When the attachment device 56 is installed in the patient's oral cavity, the second section 60 extends outwardly from the lower archwire 30 in a lateral direction. Preferably, the second section 60 extends outwardly from the lower archwire 30 in a direction that is at an angle relative to the occlusal plane of the patient. This angle is represented by the letter "C" in FIG. 3.

Optionally, the angle "C" may be determined by reference to an upper side of the passage 62 of the attachment device 56 in instances where the upper side is substantially parallel to the occlusal plane of the patient. Preferably, the angle "C" is in the range of about 30 degrees to about 90 degrees. More preferably, the angle "C" is in the range of about 45 degrees to about 60 degrees.

As can be best appreciated by reference to FIG. 1, the second section 60 extends away from the first section 58 in a direction that lies between a gingival direction and a buccolabial direction (i.e., an angle between 90 degrees and zero degrees) relative to the patient's lower dental arch 24. Preferably, the angle "C" is selected so that the interarch appliance does not contact the components of the orthodontic system 26 that are mounted on the patient's lower dental arch 24. In addition, the angle "C" is selected so that unnecessary interference is avoided between the interarch appliance 40 and the adjacent soft tissue inside the oral cavity, such as the soft tissue near the patient's lips and cheeks.

The attachment device 56 may be made by any one of a number of suitable manufacturing techniques, including a machining, casting or metal injection molding technique. Optionally, the attachment device 56 is made of stainless steel such as series 300 (for example, AISI type no. 316).

In use, the attachment device 56 is threaded onto the lower archwire 30 before the lower archwire 30 is positioned in the slots of the lower brackets 28. In FIG. 1, the attachment device 56 is positioned between the patient's lower left cuspid tooth and the patient's lower left first bicuspid tooth. Next, the archwire 30 is placed into the slots of the lower brackets 28 as well as into the passage of the lower buccal tube 32. The ligatures are then placed around each of the lower brackets 28 in order to seat the archwire 30 in the slots of the brackets 28. The outer end of the archwire 30 is then bent at an angle at a location distal of the lower buccal tube.

The attachment device 56 may be coupled by an additional section of wire (not shown) to the lower buccal tube 32 if desired. This step is optional, but can be used to prevent the attachment device 56 from sliding in a mesial direction along the lower archwire 30 and bearing against the bracket 28 that is mounted on the patient's lower left cuspid tooth. A section of metallic wire, tied in a loop extending around the lower buccal tube 32 and the attachment device 56, is useful in such instances.

The upper connector 50 of the interarch appliance 40 is connected to the upper buccal tube 38 by insertion of the pin 52 into the auxiliary passage of the upper buccal tube 38. The outer end of the pin 52 is then bent in an arc having a "U"-shaped configuration as shown in FIG. 1 in order to secure the pin in place. The first member 42 of the interarch appliance 40 is preferably removed from the second member 44 during such installation.

Next, the connector 54 of the first member 42 is coupled to the attachment device 56 by placing the hook-shaped portion of the connector 54 through the opening 64. The connector 54 is then crimped, so that the open hook-shaped configuration of the connector 54 is modified to a generally closed loop configuration as illustrated in FIG. 1. The closed loop need not be completely closed, but should be sufficiently closed so that disengagement of the connector 54 from the second section 60 does not occur during treatment.

Next, and while the patient's jaws are opened, the second and third members 44, 46 are urged together against the outward force presented by the coil spring 48, and the end of the first member 42 remote from the connector 54 is placed into the passageway of the second member 44. Once the members 44, 46 are released, the spring 48 expands and the appliance 40 is retained in place. Optionally, the length of the first member 42 may be selected so that the spring 48 is fully compressed when the patient's jaws are closed and yet does not advance the lower dental arch 24 in a non-yielding manner.

Further details, additional options and installation techniques of the interarch appliance 40 may be obtained by reference to applicant's co-pending U.S. patent application Ser. No. 09/912,911, entitled "MECHANISM WITH FORMED STOP FOR LIMITING RELATIVE MOVEMENT" filed Jul. 25, 2001, applicant's presently pending U.S. patent application Ser. No. 09/687,392, entitled "COUPLING FOR ORTHODONTIC APPLIANCE" and filed on Oct. 13, 2000 and the aforementioned U.S. Pat. No. 5,964,588.

FIG. 1 as well as the paragraphs set out above describe the assembly 20 as it appears on the left-hand side of the patient's dental arches. However, it should be understood in this regard that the assembly 20 preferably includes similar or identical components on the right-hand side of the patient's dental arches. Specifically, the assembly 20 as exemplified in FIG. 1 preferably includes two interarch appliances 40, two attachment devices 56 as well as other components (such as additional brackets and buccal tubes) that are similar or identical to the same components shown in FIG. 1.

A number of variations are possible. For example, the interarch appliance could be another type of interarch appliance, such as a Herbst-appliance that lacks a spring. As another possibility, the connector 54 may be modified by providing a pair of opposed arms having a somewhat "L"-shaped configuration which together, when closed, provide a hook-shaped configuration (i.e., closed-hook) for coupling to the second section 60 of the attachment device 56. An example of such opposed arms is described in the aforementioned U.S. Pat. No. 5,964,588. As used herein, "hook-shaped" shall mean any shape that extends through the opening 64 to hook onto the second section 60.

Moreover, the brackets, buccal tubes and other components of the assembly may be different than those shown in FIG. 1. For example, the brackets may be self-ligating brackets as are commonly known in the art. The brackets may be "twin" tiewing brackets, "single" tiewing brackets or any other type of brackets as may be desired and may be made of metal, plastic, ceramic, etc.

FIGS. 5–7 illustrate an attachment device 56' according to another embodiment of the invention. The attachment device 56' is somewhat similar to the attachment device 56 described above, except for the differences as set out below. Consequently, a description of the common aspects need not be repeated.

The attachment device 56' has a somewhat overall "U"-shaped configuration when viewed in end view as shown in FIG. 6. The attachment device 56' includes a first section 58' with a first part 70' and a second part 72' that is opposed from the first part 70'. The first part 70' and the second part 72' are pivotally movable toward and away from each other, and are shown in their open configuration in FIGS. 5–7. When the first part 70' and the second part 72' are moved toward each other, the attachment device 56' has a configuration that resembles the attachment device 50 shown in FIGS. 1–4.

When the first part 70' and the second part 72' are moved away from each other to an open configuration as shown in FIGS. 5–7, an entryway 74' is presented. The entryway 74' enables the practitioner to move the attachment device 56' around an archwire (such as the lower archwire 30) such that the archwire 30 is moved into passage 62' in a lateral direction. Such construction is useful in instances where the lower archwire 30 has been previously ligated to the lower brackets 28.

Once the lower archwire 30 is in place in the passage 62', the first part 70' and the second part 72' are moved toward each other to close the entryway 74' and render the first section 58' non-rotatable with respect to the archwire 30. Preferably, but not necessarily, the attachment device 56' is made of a fully annealed material that is bent past its yield point when the parts 70', 72' are moved either toward or away from each other. As such, the attachment 56' will tend to stay in either its open or closed configuration as desired.

Optionally, the attachment device 56' has a second section with a single part or loop. As another option, and as shown in FIGS. 5–7, the attachment device 56' has a second section 60' that includes a first part 76' and a second part 78', each of which includes a loop. In this embodiment, the parts 70', 76' are adjacent and directly connected to each other, the parts 72', 78' are adjacent and directly connected to each other, and the parts 70', 72' are adjacent and directly connected to each other. When the parts 70', 72' are moved together to close the entryway 74', the first and second parts 76', 78' overlay each other and present a single loop, such as the loop-shaped configuration of the second section 60 shown in FIGS. 2–4. Each of the parts 76', 78' includes an opening, and the openings are preferably coaxial with each other once the entryway 74' is closed.

Moreover, once the connector 54 of the interarch appliance 40 is secured to the second section 60' and is cinched or bent to a closed-loop configuration, the connector 54 tends to prevent the first and second parts 76', 78' from moving away from each other. Such construction helps ensure that the entryway 74' will not inadvertently open and/or allow the first section 58' to rotate on the archwire 30 during the course of orthodontic treatment.

Figure 8:
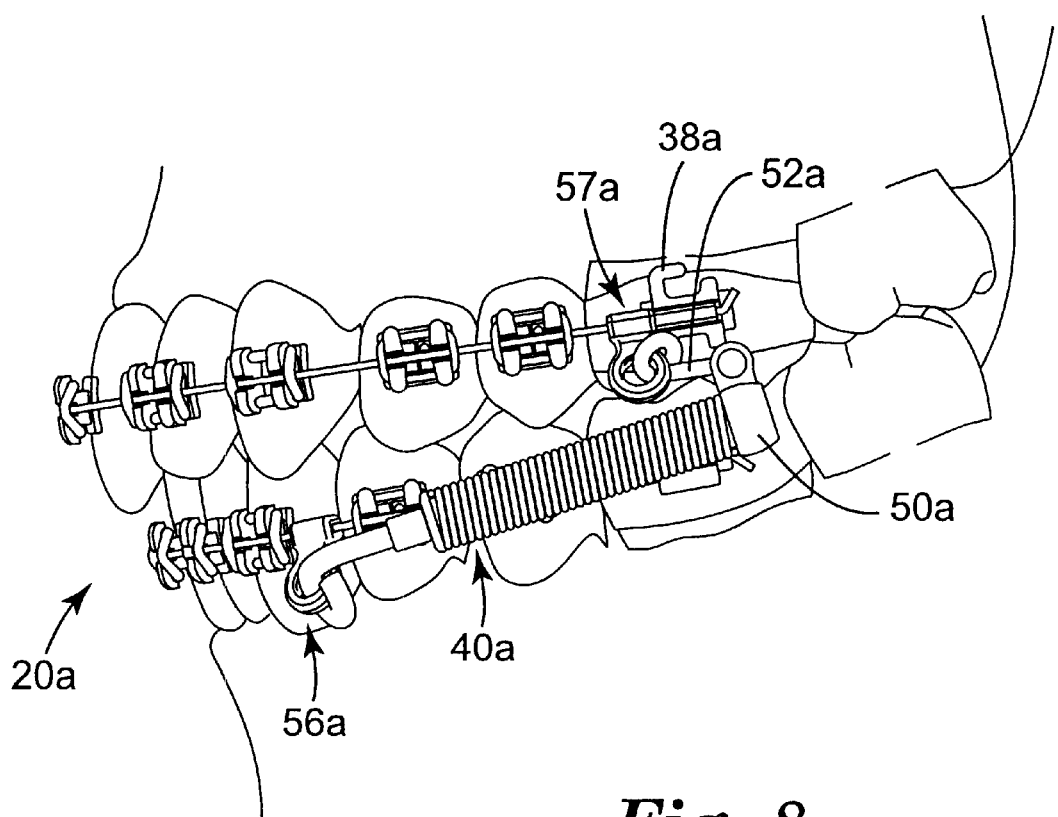
FIG. 8 is a side elevational view of an exemplary upper and lower dental arch of a patient undergoing orthodontic treatment that is somewhat similar to the view shown in FIG. 1, except that FIG. 8 illustrates an orthodontic assembly according to another embodiment of the invention.

FIG. 8 is an illustration of an assembly 20a according to another embodiment of the invention. Except as described below, the assembly 20a is identical to the assembly 20 as set out above.

An interarch appliance 40a of the assembly 20a includes an upper connector 50a that is connected to a pin 52a. In turn, the pin 52a is pivotally coupled to an attachment device 57a that is located on a mesial side of an upper buccal tube 38a. As shown in FIG. 8, an outer end of the pin 52a extends through an opening of the attachment device 57a and is bent to a closed-loop configuration.

Preferably, the attachment device 57a is identical to the attachment device 56 or 56' described above (as is another attachment device 56a that is located on the patient's lower dental arch). However, the upper attachment device 57a is preferably oriented so that it extends at an angle that lies between an occlusal direction and a buccolabial direction relative to the teeth of the patient's upper dental arch. Such construction is an advantage, in that the same component may be used in both locations. Furthermore, the use of the attachment device 57a is particularly beneficial in instances where the upper buccal tube (such as buccal tube 38a) does not contain an auxiliary passage that could be otherwise used for receiving the pin 52a.

Figure 9:
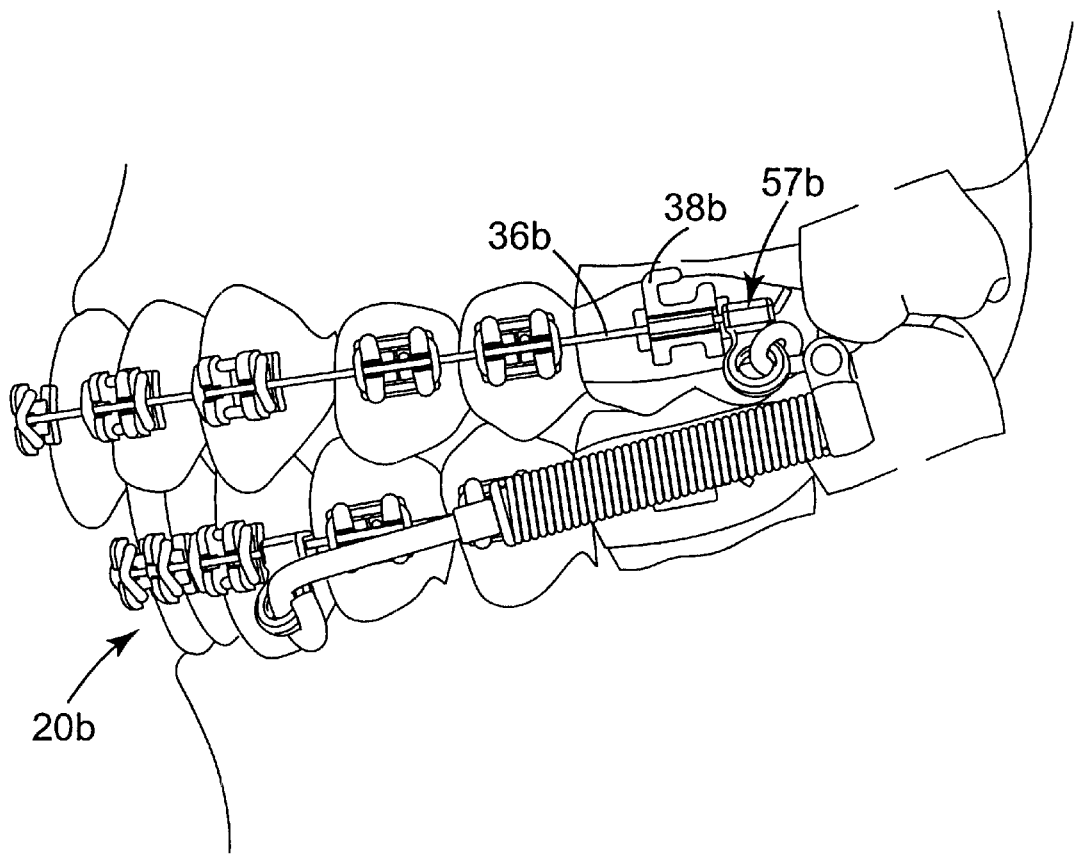
FIG. 9 is a view somewhat similar to FIGS. 1 and 8 except that FIG. 9 depicts an orthodontic assembly that is constructed in accordance with an additional embodiment of the invention.

An orthodontic assembly 20b according to another embodiment of the invention is illustrated in FIG. 9. The assembly 20b is essentially the same as the assembly 20a except for the differences mentioned below. As shown in FIG. 9, the assembly 20b includes an attachment device 57b. However, the attachment device 57b is located on the distal side of an upper buccal tube 38b. A bend placed in the distal end of an archwire 36b serves to retain the attachment device 57b in place.

Figure 10:
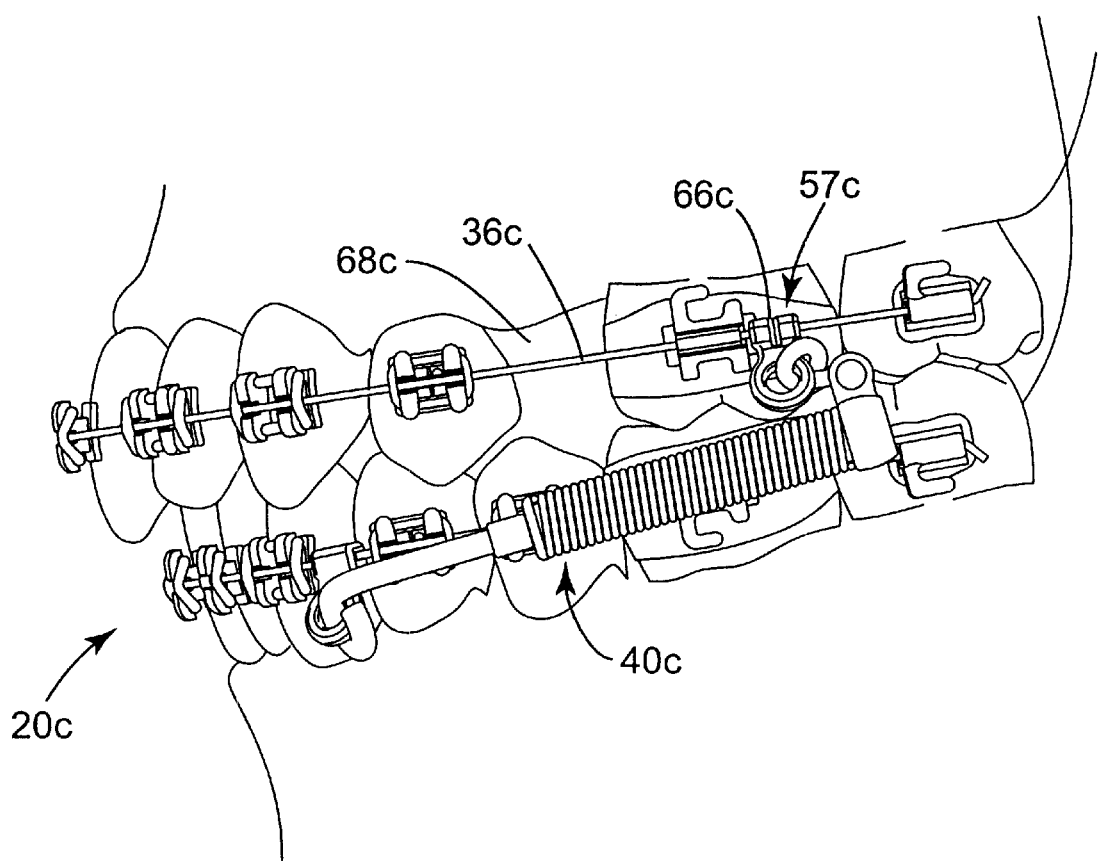
FIG. 10 is a view somewhat similar to FIGS. 1, 8 and 9 except that FIG. 10 illustrates an orthodontic assembly constructed in accordance with a further embodiment of the invention.

An orthodontic assembly 20c according to another embodiment of the invention is illustrated in FIG. 10. In this embodiment, an upper attachment device 57c of the assembly 20c is crimped to an upper archwire 36c so that sliding movement of the attachment device 57c along the length of the upper archwire 36c is precluded. Optionally, the attachment device 57c includes a groove 66c to receive the jaws of a crimping tool such as a pair of dull orthodontic cutters. The groove 66c serves to hold the jaws of the tool in place during the time that a force is exerted on the attachment device 57c in order to crimp the attachment device 57c to the archwire 36c.

The assembly 20c is particularly useful for closing a space in the upper dental arch, such as space 68c. The space 68c may be present, for example, in instances where a tooth has been extracted. In those instances, the interarch appliance 40c is used to exert a rearwardly directed force on the upper archwire 36c that, in turn, tends to push the patient's anterior teeth in a distal or rearwardly direction. Over a period of time, the space 68c will become smaller and will preferably close in order to enable the patient's dentition to present a more aesthetic appearance.

Figure 11:
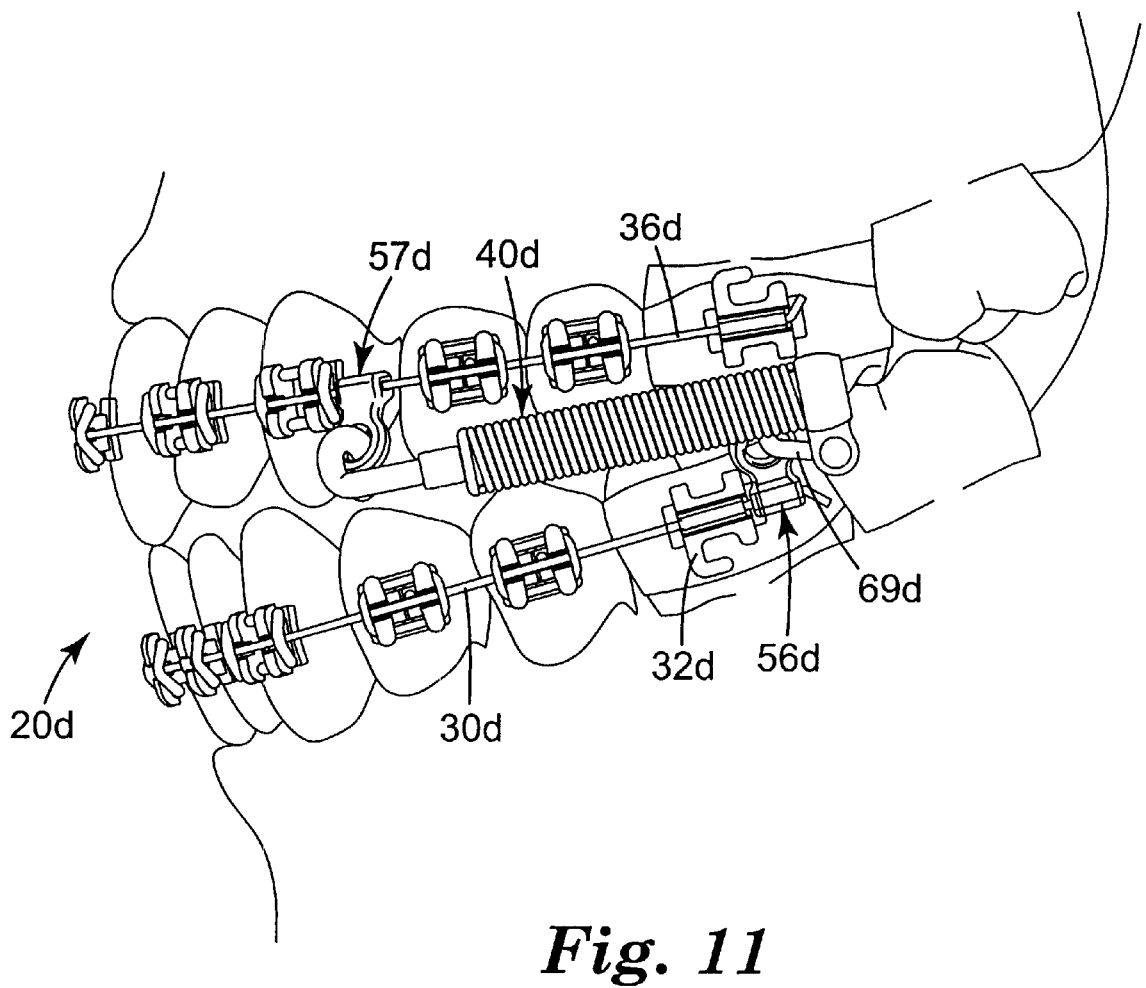
FIG. 11 is a view somewhat similar to FIGS. 1 and 8–10 except that FIG. 11 shows an orthodontic assembly that is constructed in accordance with yet another embodiment of the invention.

An orthodontic assembly 20d according to another embodiment of the invention is shown in FIG. 11. The assembly 20d includes an interarch appliance 40d that is preferably similar or identical to the interarch appliance 40 described above. However, the assembly 20d as shown in FIG. 11 is particularly useful for correcting a Class III malocclusion, or a malocclusion where the patient's lower dental arch is located in a position that is considered an excessive distance forward in comparison to the location of the upper dental arch.

The assembly 20d includes a lower attachment device 56d as well as an upper attachment device 57d. The lower attachment device 56d is located on a distal side of a lower buccal tube 32d. An outer end section of the lower archwire 30d is bent in an arc in order to retain the lower attachment device 56d in place.

The upper attachment device 57d is located along the upper archwire 36d at a location between the patient's upper left cuspid and the patient's upper left first bicuspid tooth. The upper attachment device 57d has a second section that extends at an angle between an occlusal direction and a buccolabial direction. The upper attachment device 57d receives a first member of the interarch appliance 40d that is optionally the same as the interarch appliance 40 described above.

The lower attachment device 56d has a second section that also extends at an angle that is located between an occlusal direction and a buccolabial direction. The interarch appliance 40d includes a third member with an outer connector. A pin 69d (similar to pin 52) extends through a hole in the connector and through an opening of the lower attachment device 56d. The pin 69d has an outer end section that is bent in a closed-loop configuration in order to secure the pin 69d to the lower attachment device 56d.

In use, the outwardly-directed force exerted by the coil spring of the interarch appliance 40d tends to urge the components of the orthodontic system mounted on the patient's upper dental arch in a direction away from the components of the orthodontic system mounted on the patient's lower dental arch. Over a period of time, such a force tends to slowly move the upper dental arch in a forward direction and the lower dental arch in a rearward direction such that Class I occlusion is eventually achieved.

Figure 12:
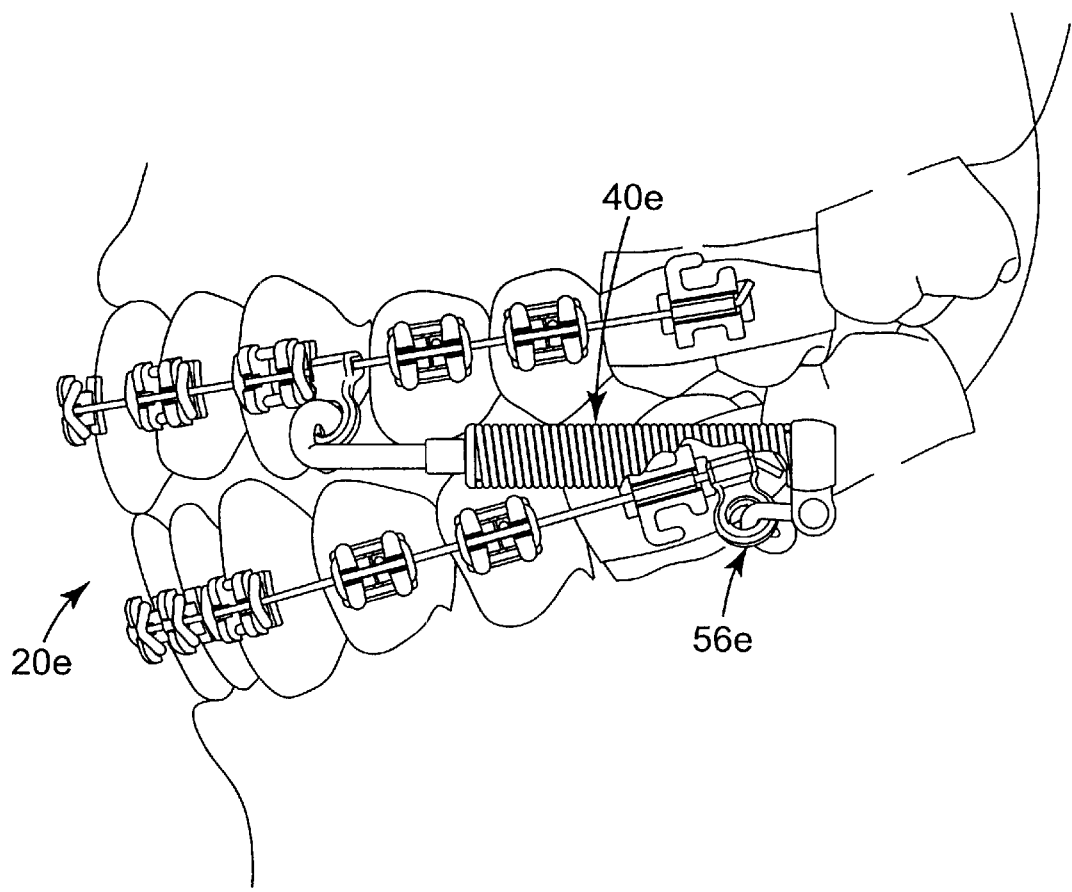
FIG. 12 is a view somewhat similar to FIGS. 1 and 8–11 except that FIG. 12 shows an orthodontic assembly according to an additional embodiment of the invention.

An orthodontic assembly 20e according to another embodiment of the invention is illustrated in FIG. 12. The assembly 20e is essentially the same as the assembly 20d depicted in FIG. 11 except for the differences as noted below.

An attachment device 56e of the assembly 20e is similar to the attachment device 56d, except that the attachment device 56e has a second section that extends outwardly from the lower archwire in a direction that is between a gingival direction and a buccolabial direction. Optionally, the attachment devices 56d and 56e are identical, except that the attachment device 56e has been inverted so that its second section extends in a different direction. In FIG. 12, a portion of interarch appliance 40e has been cut away for purposes of illustration in order to show the location and orientation of the lower attachment device 56e.

Those skilled in the art may recognize that a number of variations may be made to some or all of the components of the orthodontic assembly as described above without departing from the essence of the invention. Furthermore, other methods of installing the assembly are possible. As such, the present invention should not be deemed limited to the specific examples that are described in detail above, but instead only by a fair scope of the claims that follow along with their equivalents.

What is claimed is:

1. An orthodontic assembly comprising:
    an orthodontic system including a set of brackets and an elongated archwire connected to the brackets;
    an interarch appliance for repositioning the lower dental arch relative to the upper dental arch, the interarch appliance including a coupler having an arm; and
    an attachment device connected to the orthodontic system, the attachment device including a body having a first section and a second section, the first section having a passage with a rectangular cross-sectional configuration for receiving the archwire, wherein the first section is substantially non-rotatable relative to the archwire in direction about the length of the archwire, wherein the second section includes an opening that pivotally receives the arm of the coupler, wherein the passage has a central axis, wherein the opening has a central axis that extends in non-parallel and non-intersecting relationship to the central axis of the passage, wherein the passage has an upper side that generally extends in the occlusal plane of the patient when the device is in use in the oral cavity, and wherein the second section generally extends along a path away from the central axis that is at a certain angle relative to the upper side, and wherein the angle lies between a gingival direction and a buccolabial direction relative to the patient's lower dental arch when the device is in use in the oral cavity.

2. An orthodontic assembly according to claim 1 wherein the opening is substantially circular.

3. An orthodontic assembly according to claim 1 wherein the central axis of the opening extends in a direction that is generally perpendicular to the central axis of the passage.

4. An orthodontic assembly according to claim 1 wherein the body has an entryway into the passage for receiving the archwire in directions laterally of the central axis of the passage, and wherein the entryway can be closed after the archwire is received in the passage.

5. An orthodontic assembly according to claim 1 wherein the angle is in the range of about 30 degrees to about 90 degrees.

6. An orthodontic assembly according to claim 1 wherein the angle is in the range of about 45 degrees to about 60 degrees.

7. An orthodontic assembly according to claim 1 wherein the first section includes a first part extending along a portion of the passage and a second part extending along another portion of the passage, wherein the first part is connected to the second part for pivotal movement toward and away from the second part, and wherein the first part and the second part present an entryway into the passage when the first part is moved away from the second part, and wherein the entryway is generally closed when the first part is moved toward the second part.

8. An orthodontic assembly according to claim 7 wherein the first section is a unitary component made of a fully annealed material that is bent past its yield point when the first part is moved toward the second part.

9. An orthodontic assembly according to claim 1 wherein the interarch appliance includes a first member and a second member, wherein the second member has a tubular configuration, and wherein the first member has a portion slidably received in the second member.

10. An orthodontic assembly according to claim 9 wherein the interarch appliance also includes a third member having a tubular configuration, wherein a portion of the second member is slidably received in the third member.

11. An orthodontic assembly according to claim 1 wherein the arm of the coupler has a generally hook-shaped configuration.

12. An orthodontic assembly comprising:
an orthodontic system including a set of brackets and an elongated archwire connected to the brackets;
an interarch appliance for repositioning the lower dental arch relative to the upper dental arch, the interarch appliance including a coupler having an arm; and
an attachment device connected to the orthodontic system, the attachment device including a body having a first section and a second section, the first section having a passage receiving the archwire, wherein the first section is substantially non-rotatable relative to the archwire in direction about the length of the archwire, wherein the first section includes a first part extending along a portion of the passage and a second part extending along another portion of the passage, wherein the first part is connected to the second part for pivotal movement toward and away from the second part, wherein the first part and the second part present an entryway into the passage when the first part is moved away from the second part, wherein the entryway is generally closed when the first part is moved toward the second part, wherein the second section includes an opening that pivotally receives the arm of the coupler, wherein the second section includes a first part and a second part, wherein the first part of the second section is connected to the first part of the first section, wherein the second part of the second section is connected to the second part of the first section, and wherein each of the first part of the second section and the second part of the second section have a hole that together present the opening.

13. An orthodontic assembly according to claim 12 wherein the first part of the second section is remote from the second part of the second section when the first part of the first section is moved away from the second part of the first section.

14. An orthodontic assembly according to claim 12 wherein the first section and the second section are made from a fully annealed material as a unitary component.

15. An orthodontic attachment device comprising a body having a first section and a second section connected to the first section, the first section having a passage with a central axis and a generally rectangular cross-sectional configuration in reference planes perpendicular to the central axis for non-rotatably receiving an archwire, the second section extending away from the central axis in a generally perpendicular direction and having an opening, the second section including a peripheral edge segment that surrounds the opening for connection to an appliance, wherein the passage has a central axis, wherein the opening has a central axis that extends in non-parallel and non-intersecting relationship to the central axis of the passage, wherein the passage has an upper side, and wherein the second section generally extends along a path away from the central axis that is at an angle greater than zero and less than ninety degrees relative to the upper side.

16. An orthodontic attachment device according to claim 15 wherein the central axis of the opening extends in a direction that is generally perpendicular to the central axis of the passage.

17. An orthodontic attachment device according to claim 15 wherein the passage has an upper side that generally extends in the occlusal plane of the patient when the device is in use in the oral cavity, and wherein the second section generally extends along a path away from the central axis that is at a certain angle relative to the upper side.

18. An orthodontic attachment device according to claim 17 wherein the angle is in the range of about 30 degrees to about 90 degrees.

19. An orthodontic attachment device according to claim 17 wherein the angle is in the range of about 45 degrees to about 60 degrees.

20. An orthodontic attachment device according to claim 15 wherein the first section includes a first part extending along a portion of the passage and a second part extending along another portion of the passage, wherein the first part is connected to the second part for pivotal movement toward and away from the second part, and wherein the first part and the second part present an entryway into the passage when the first part is moved away from the second part, and wherein the entryway is generally closed when the first part is moved toward the second part.

21. An orthodontic attachment device according to claim 20 wherein the second section includes a first part and a second part, wherein the first part of the second section is connected to the first part of the first section, wherein the second part of the second section is connected to the second part of the first section, and wherein each of the first part of the second section and the second part of the second section have a hole that together present the opening.

22. A method of connecting a dental arch repositioning appliance to an orthodontic system that includes a set of brackets and an elongated archwire connected to the brackets, the method comprising:
placing an archwire in a passage having a rectangular cross-section of an attachment device in an orientation such that the device generally extends outwardly from the archwire;
coupling the device to a segment of an archwire such that the device is substantially non-rotatable relative to the longitudinal axis of the archwire at an angle between a gingival direction and a buccolabial direction relative to the patient's lower dental arch; and
pivotally connecting an outer section of the device to the repositioning appliance by extending a connector of the repositioning appliance through an opening of the attachment device, wherein the opening has a central axis that is non-parallel to the archwire segment.

23. A method of connecting a dental arch repositioning appliance to an orthodontic system according to claim 22 wherein the act of placing the archwire in the passage of an attachment device and the act of coupling the device to the archwire are carried out simultaneously.

24. A method of connecting a dental arch repositioning appliance to an orthodontic system according to claim 22 wherein the act of placing an archwire in a passage of an attachment device includes the act of moving the archwire through an entryway into the passage that extends along one side of the passage.

25. A method of connecting a dental arch repositioning appliance to an orthodontic system according to claim 22 wherein the act of coupling the device to the archwire is carried out by closing an entryway to the passage that extends along one side of the passage.

* * * * *